United States Patent
Plank et al.

(10) Patent No.: US 7,766,654 B2
(45) Date of Patent: Aug. 3, 2010

(54) DEVICE AND METHOD FOR DETERMINING AND CONTROLLING THE DEGREE OF POLYMERIZATION OF POLYMERIZABLE DENTAL MATERIAL

(75) Inventors: Wolfgang Plank, Rankweil (AT); Reinhard Goerge, Lindau (DE)

(73) Assignee: Ivoclar Vivadent AG, Schaan (LI)

( * ) Notice: Subject to any disclaimer, the term of this patent is extended or adjusted under 35 U.S.C. 154(b) by 1140 days.

(21) Appl. No.: 11/402,363

(22) Filed: Apr. 7, 2006

(65) Prior Publication Data

US 2006/0240376 A1 Oct. 26, 2006

(30) Foreign Application Priority Data

Apr. 26, 2005 (DE) ............ 10 2005 019 386

(51) Int. Cl.
*A61C 3/00* (2006.01)
*A61N 5/06* (2006.01)
*C08F 2/48* (2006.01)

(52) U.S. Cl. ............... 433/29; 250/504 R; 250/504 H; 522/182; 522/908

(58) Field of Classification Search .......... 433/29; 606/3, 11; 250/504 R, 504 H; 522/182, 522/908
See application file for complete search history.

(56) References Cited

U.S. PATENT DOCUMENTS

| | | |
|---|---|---|
| 4,538,070 A | 8/1985 | Herold |
| 5,007,837 A | 4/1991 | Werly |
| 5,198,678 A * | 3/1993 | Oppawsky ............ 250/455.11 |
| 5,298,758 A | 3/1994 | Tateosian |
| 5,306,144 A | 4/1994 | Hibst |
| 5,503,559 A | 4/1996 | Vari |
| 5,738,678 A | 4/1998 | Patel |
| 5,922,605 A | 7/1999 | Feurstein |
| 6,386,865 B1 | 5/2002 | Suh |
| 2001/0029009 A1 | 10/2001 | Jung |
| 2002/0014864 A1 | 2/2002 | Gemunder |

FOREIGN PATENT DOCUMENTS

| | | |
|---|---|---|
| DE | 38 29 817 A1 | 3/1990 |
| DE | 42 00 741 C2 | 7/1993 |
| EP | 0 511 554 A1 | 11/1992 |
| EP | 0 563 953 A2 | 10/1993 |
| EP | 0 993 810 A2 | 4/2000 |
| EP | 1 236 444 A1 | 9/2002 |
| EP | 1 281 370 A2 | 2/2003 |
| WO | WO 02/062420 A1 | 8/2002 |
| WO | WO 2005/057670 A2 | 6/2005 |
| WO | WO 2006/014402 | 2/2006 |

\* cited by examiner

*Primary Examiner*—Fred M Teskin
(74) *Attorney, Agent, or Firm*—John C. Thompson; Alan S. Korman; Sandra J. Thompson

(57) ABSTRACT

A device (10) and method for determining and controlling the degree of polymerization of polymerizable dental material (14), which device includes a light and/or heat source (18 or 20), with which the dental material (14) is impinged. The device further includes a control device (26) and a sensor (24) connected to the control device (26), whereby the sensor (24) detects radiation (natural radiation) emitted from the dental material (14) of a predetermined wavelength.

19 Claims, 5 Drawing Sheets

DEVICE AND METHOD FOR DETERMINING AND CONTROLLING THE DEGREE OF POLYMERIZATION OF POLYMERIZABLE DENTAL MATERIAL

CROSS-REFERENCE TO RELATED APPLICATIONS

This application claims foreign priority benefits under 35 U.S.C. §119 from German patent application Ser. No. 10 2005 019 386.2 filed Apr. 26, 2005.

TECHNICAL FIELD

The invention relates to a system for determining and controlling the degree of polymerization of polymerizable dental material, and more particularly in a preferred embodiment to a system which includes a light and/or heat source for polymerization and a sensor which detects mid wavelength infrared radiation emitted by the dental material during polymerization.

BACKGROUND OF THE INVENTION

It has long been known to impinge materials with suitable radiation, for example thermal radiation, and to detect the reflected amount of light from the respective material via a sensor. One example of this is the solution disclosed in European patent application 0 563 953 A2. A disadvantage of this solution is that the light detections depend heavily on the surface characteristics of the material. Such a solution is not suitable for the impingement of dental materials, because the existing degree of moisture of the dental materials would greatly affect the degree of reflection and lead to errors in measured values.

In order to provide a reliable detection of the energy impingement in every case, that is, the impingement by means of a light and/or heat source, U.S. Pat. No. 5,922,605 discloses the use of a sensor as a light sensor. The sensor is arranged outside of the actual radiation area and measures the brightness and/or heat in the outer field of the dental material, so that the disadvantages of the previously noted solution are avoidable.

On the other hand, the polymerization of the dental material used depends heavily on numerous factors. For example, polymerization of typical surface layers is faster than deeper layers of the dental material, which is used in dental restoration, for example.

For determining which polymerization time is favorable, it has been proposed already to determine the mass of the polymerization material and to adjust the polymerization time in dependence thereon. Also, numerous further features have been proposed in order to prevent a release of monomers with free radicals, caused by incomplete polymerization, as well as the formation of edge gaps of the dental restoration caused by an excessive polymerization time.

Not only different dental materials, but also, for example, parameters in individual cases affect the polymerization process, such as for example the storage time of the dental material before the application. In order to achieve an optimal polymerization result, one must realize practically an assay-polymerization with precisely the same form from the same charge of the polymerization material. This then will demonstrate and determine how the polymerization time should be adjusted. This method, naturally, is not practical.

OBJECTS AND SUMMARY OF THE INVENTION

Therefore, the present invention is based on the object of providing a device for determining the degree of polymerization of polymerizable dental material, as well as a corresponding method, which offers an optimal polymerization result, without requiring additional expense.

According to the invention, it is particularly favorable that the radiation emitted from the dental material itself is detected. Therefore, errors caused by reflections and the like are excluded from the start, whereby it should be understood that by a suitable selection of the optical axis of the detection radiation and the impingement radiation, it can be ensured that errors in the measurement results do not occur from other radiation effects, such as, for example, interferences or the like.

According to the invention, it is particularly favorable that the selection of the wavelengths and wavelength ranges of the detection radiation and the impingement radiation is adaptable in broad ranges to the requirements. For example, the impingement radiation can cover the range of long range ultraviolet and violet light and/or near infrared light, while the wavelength range of the radiation detected by the sensor, for example, can lie above 3000 nm in the mid wavelength infrared range, so that a defined distance between the wavelengths and the frequencies exists.

According to the invention, it is especially favorable that by means of the photo-thermal detection of the polymerization material, the polymerization degree can be determined exactly, and indeed, pattern-specific, that is, as a function of the actual impinged dental mass.

Therefore, despite the elimination of an assay-polymerization, it is possible to determine the degree of polymerization and therewith, the switch-off timepoint and/or the polymerization cycle, that is, to determine exactly the temporal course of the energy impingement for the polymerization.

The energy impingement with the polymerization radiation can be adapted in broad ranges to the requirements or the desired polymerization results. For example, the light or heat source can be modulated in the temporal course with a square-wave pulse signal, which can readily be represented by LED- or laser diodes.

According to the present invention, it is especially favorable that the interference effects, which can produce different polymerization results, can be compensated: if for example in a moist surface, the surface of the dental material is heavily reflective for the impingement radiation, so that the polymerization radiation contacting the dental material has less intensity, then the detection radiation emitted from the dental material likewise is less in a corresponding manner, so that the actual degree of polymerization can be determined in-situ.

The detection radiation can be conducted in any suitable manner to the sensor. When using a hand-held device, the impingement radiation and the detection radiation can be conducted by a photo conducting rod and then with a suitable separating device, such as a mirror, which is inclined at an angle of approximately 45° and is penetrable by the impingement radiation, is reflected for the detection radiation to provide a beam division. With a stationary device, it is favorable to arrange the light and/or heat source of the sources at a location that is spatially offset relative to the sensor or sensors. For example, a sensor can be oriented perpendicular to the surface, while two radiation sources impinge the surface of the dental material at an angle of 30°, for example.

It should be understood that it is expedient if the sensor is protected from interference effects, or these are compensated. With pressure-sensitive sensors, for example, a reference sensor can be provided, which is not impinged by the detection radiation, and which is arranged in a measurement bridge together with the active sensor, in order to prevent measurement errors. It also should be understood that the sensor can be calibrated in a suitable manner when exact results are desired.

According to the present invention, it is particularly favorable that the polymerization is determinable exactly as an exothermic reaction and that this effect can be used in a surprisingly simple manner for determining the degree of polymerization.

In a further advantageous embodiment, it is provided that the wavelength range of the polymerization radiation and the detection radiation emitted from the dental material differ at least fractionally from one another.

In a further advantageous embodiment, it is proposed that the polymerization radiation emitted from the light and/or heat source on the dental material lies at least partly in a wavelength range between 350 nm and 550 nm and that the sensor radiation during a polymerization cycle is detectable.

In a further advantageous embodiment, it is provided that with the sensor, the temperature of the detection radiation can be determined and with the control device, its temporal course can be determined; in particular, the temperature increase and/or temperature decrease can be evaluated.

In a further advantageous embodiment, it is provided that the optical axes of the source and the sensor extend at an angle deviating from zero relative to the dental material, and in particular is sensitive in an intra-oral area and is oriented on the dental material.

In a further advantageous embodiment, it is provided that the sensor and/or the control device is integrated in the device and that the device has multiple polymerization areas, in which dental material can be polymerized, and that a sensor, in particular, multiple sensors, are oriented onto each polymerization area.

In a further advantageous embodiment, it is provided that the polymerization areas are spatially separated from one another and that in each polymerization area, at least one light and/or heat source is disposed.

In a further advantageous embodiment, it is provided that between at least one sensor and the dental material, at least one photo conducting element is arranged, with which detection radiation from the dental material area can be conducted to the sensor and/or with which impingement radiation can be conducted from the light and/or heat source to the dental material.

In a further advantageous embodiment, it is provided that at least one optical fiber extends over a part of the entire length of the photo conducting element, and in particular, has a light outlet on the side, which faces the sensor.

In a further advantageous embodiment, it is provided that the photo conducting element arranged between the dental material and its polymerization area, on the one hand, and the sensor and/or the light and/or heat source, on the other hand, has at least one optical fiber, which extends over the entire length of the photo conducting element.

In a further advantageous embodiment, it is provided that the light conducting element has at least one optical fiber, with which the detection radiation can be conducted, and that the detection-optical fiber is arranged in a central region or in a peripheral region of the photo conducting element. It is proposed further that the photo conducting element has multiple optical fibers, and that with at least one optical fiber, the detection radiation can be conducted. The detection-optical fiber is arranged, in particular, in the peripheral region of the photo conducting element.

In a further advantageous embodiment, it is provided that the light conducting element has at least one optical fiber, which is penetrable in the wavelength range of the impingement radiation, in particular, in the wavelength range of 350 to 550 nm, and that the photo conducting element has at least one optical fiber, which is penetrable in the wavelength range of the detection radiation from 800 nm to 10,000 nm, in particular from 3000 nm to 5000 nm.

In a further advantageous embodiment, it is provided that the photo conducting element is formed as a photo conducting rod, which extends between the light source and the dental material, and that the device is formed as a hand-held device. The device can be connected with an external current supply source and/or the device can have an exchangeable current supply source.

In a further advantageous embodiment, it is proposed that the light and/or heat source is formed by at least one semiconductor-energy source.

The determination of a slope of a heating curve can be recognized by the sensor. If this is steep, then the signal also could be used to reduce the light power during the polymerization cycle. If this is flat, then one could raise the light power with a corresponding signal of the sensor.

In a further advantageous embodiment, it is provided that the sensor emits a signal to the control device when the gradient of the actual parameter of the dental material changes, in particular the heating increases, and that the control device processes the output signal of the sensor and for controlling the device, in particular for controlling the light and/or heat source.

In a further advantageous embodiment, it is provided that a control signal emitted from the control device is a shut-down signal, with which the device is switched off and the polymerization process is terminated.

It is provided further that the sensor detects radiation emitted from the dental material with a wavelength of 800 nm to 10,000 nm, in particular from 3000 nm to 5000 nm.

In a further advantageous embodiment, it is provided that for detecting the radiation emitted from the dental material, the light and/or heat source is switched off temporarily by the control device during a polymerization cycle at least once.

Further advantages, details, and features are provided in the following description of several embodiments with reference to the accompanying figures.

DETAILED DESCRIPTION

Figure 1:
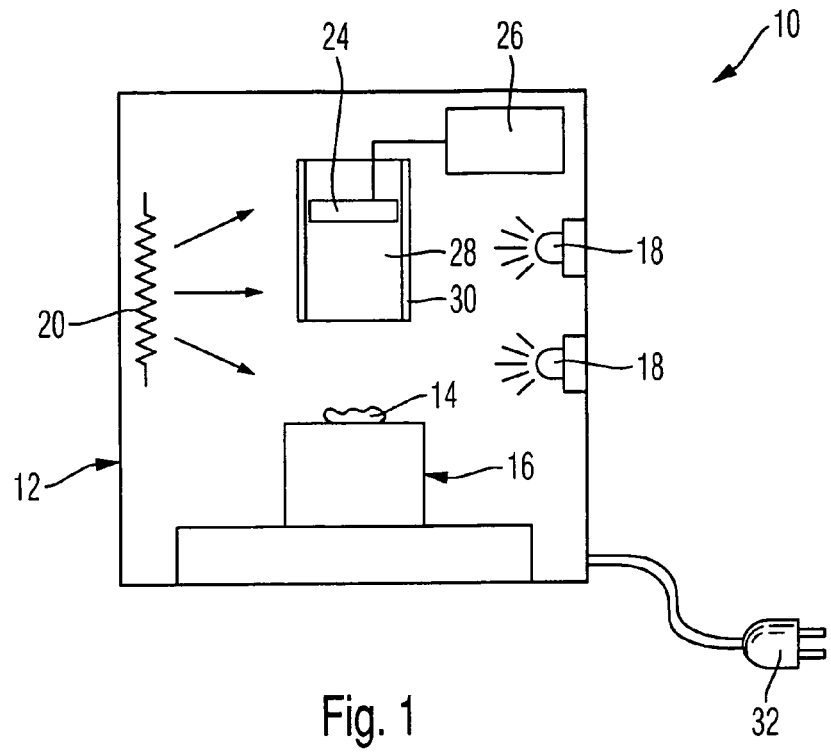
FIG. 1 shows a schematic view of a first embodiment of a device for polymerization of polymerizable dental material, according to the present invention.

The device shown in FIG. 1 has a housing 12, which is provided for accommodating the dental material 14, which takes place on a support pedestal 16.

For the polymerization of the dental material 14 in a polymerization area, which is open and impinged with radiation, a plurality of light sources 18 and/or heat sources 20 are provided, which irradiate the polymerization area with electromagnetic waves of the corresponding frequency range in the embodiment shown. The light sources 18 as well as the heat sources 20 are mounted inside on the side walls of the housing 12 in the embodiment shown. Thus, the radiation emitted from these sources does not contact the surface of the dental material perpendicularly, rather laterally at an angle from above. By the angular impingement, any large reduction of the degree of the polymerization effect of the emitted radiation by reflections is avoided.

In many cases, the surface of the polymerization area of the dental material is not flat, that is, horizontal, but is wavy, for example, or has another form. By the arrangement of multiple sources, marked negative effects on the polymerization results from reflections are prevented.

Also, when heat sources 20 and light sources 18 are shown merely on two sides of the housing, namely, right and left, as shown in the principle section in FIG. 1, it should be understood that actually a plurality of sources can be provided distributed circumferentially, and indeed, in any suitable distribution. A representation of such a distribution can be seen in U.S. Pat. No. 5,922,605 which is incorporated herein by reference.

In the embodiment shown, a sensor 24 is suspended above the dental material 14. The sensor 24 is connected with a control device 26, which controls the device 10 and in particular determines when the sources 18 and 20 are switched off or when their power should be reduced.

The sensor 24 detects the detection radiation 28 emitted from the dental material 14. In order to prevent an effect by the sources 18 and 20, the sensor is surrounded by a shield 30 in the style of an apron, whereby it should be understood that the shield 30 should not prevent the entry of the impingement radiation to the polymerization area.

The device 10 is connected via a known current supply terminal 32 and the embodiment shown forms a stationary device 12. Alternatively, it is also possible to provide an energy storage medium in the device 12, for example an accumulator, which is rechargeable via the current supply terminal 32.

Figure 2:
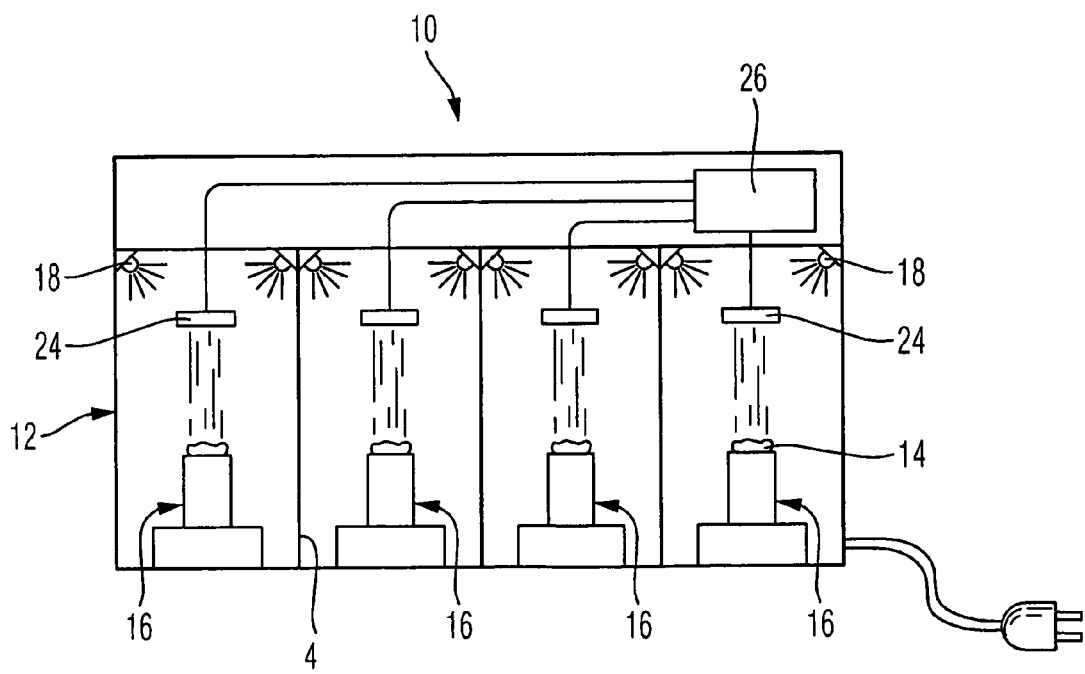
FIG. 2 shows a second embodiment of the device of FIG. 1.

FIG. 2 shows a modified form of the device 10 of the present invention. Here, the same reference numerals as used in the other figures designate the same or corresponding parts and require no further explanation. With the solution of FIG. 2, a plurality of support pedestals 16 with corresponding dental materials and polymerization areas 14 adjacent one another are provided, above which, respectively, a sensor 24 is arranged.

Above each, respective sensor 24, a light source 18 is arranged. With this arrangement, no screen or apron as shown in FIG. 1 is necessary; however, the individual polymerization areas 24 are screened from one another via intermediate walls 4.

It should be understood that instead of the linear arrangement with three intermediate walls, also in practice a two-dimensional arrangement is possible, so that, for example, a total of 16, that is four times four, dental restorations can be polymerized at the same time.

For the light sources 18 and the sensors 24, switching off can be realized depending on the existing degree of polymerization via a single central control device 26.

According to the present invention, the degree of polymerization of the dental material to be polymerized is monitored continually during the polymerization. The switching-off or the reduction of the radiation, which is supplied to the polymerization area, is controlled depending on how far the polymerization has advanced. For measurement of the degree of polymerization, surprisingly in a very simple manner, the natural radiation of the dental material is used during the polymerization.

If, for example, poly-methyl-meth-acrylate (PMMA) is used as the primary component of the dental material to be polymerized, a highly exothermic reaction during the polymerization is provided, which can be monitored easily in this regard. With such dental material, a heating exists, that is, an output of thermal radiation in the infrared region, which is detectable with the sensor of the present invention.

Figure 3:
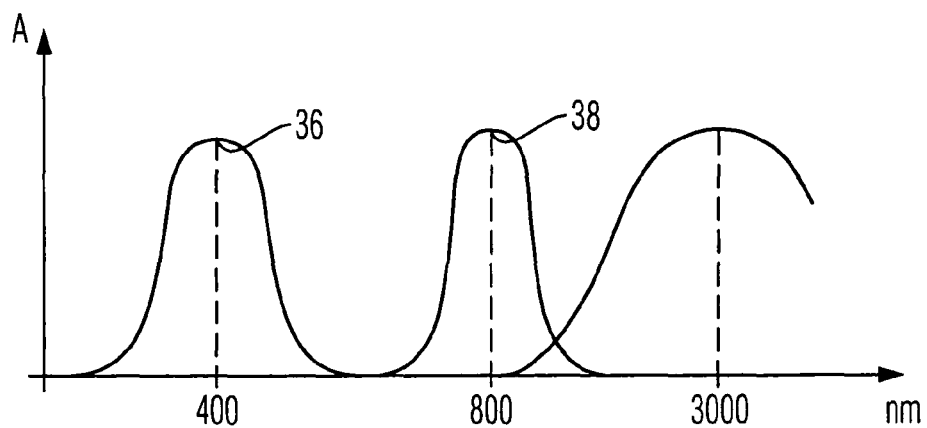
FIG. 3 shows a representation of the emission maximum of the impingement radiation and the sensitivity curve of the sensor.

In FIG. 3, a diagram for an exemplary representation of the wavelengths used is shown. The light exiting from the light sources 18 is either UV-A and/or violet and has an emission maximum 36 of approximately 400 nm in the embodiment shown. In contrast, the thermal radiation emitted from the heat sources 20 has an emission maximum 38 of 800 nm, for example lying then in the near infrared range. The maximum spectral sensitivity of the sensor used lies in the embodiment shown at approximately 3000 nm, that is, in a mid wavelength infrared range. With this selection of the wavelengths used, there is only a very minimal overlapping region between the emission curve of the heat sources 20 and the sensitivity curve of the sensor 24 as can be seen from FIG. 3.

Figure 4:
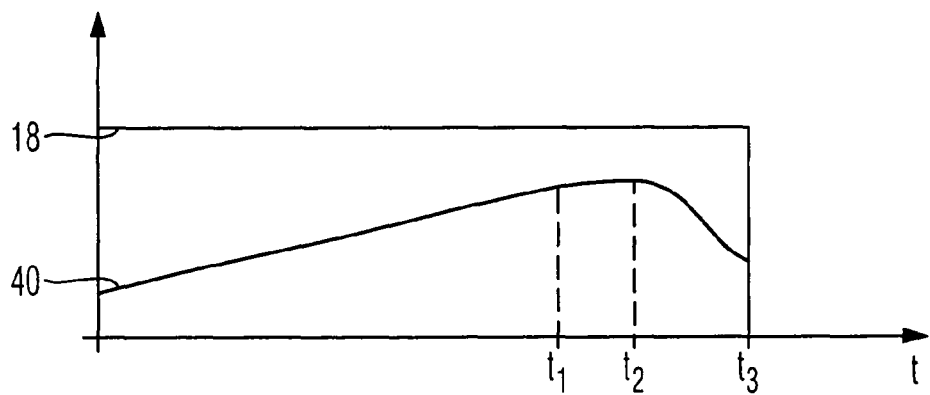
FIG. 4 shows a diagram of the temporal course of the control of the present invention.

From FIG. 4, it can be seen how the output signal 40 of the sensor can be used to control the light sources 18 via the control device 26. Over time, the radiation detected from the sensor, which produces the output signal 40, is registered.

With the switching-on of the light source 18, the sensor signal rises to the timepoint $t_1$. Up to this timepoint, the polymerization is performed with uniform polymerization progress, so that the natural radiation increases uniformly. Depending on the mass of the dental material used, however, a minimal increase up to the maximum of the natural radiation and the maximum output signal 40 of the sensor takes place earlier or later, up to the timepoint $t_2$. Subsequently, the sensor signal 40 decreases, and as soon as this is determined at timepoint $t_3$, switching-off of the light source 18 occurs.

Figure 5:
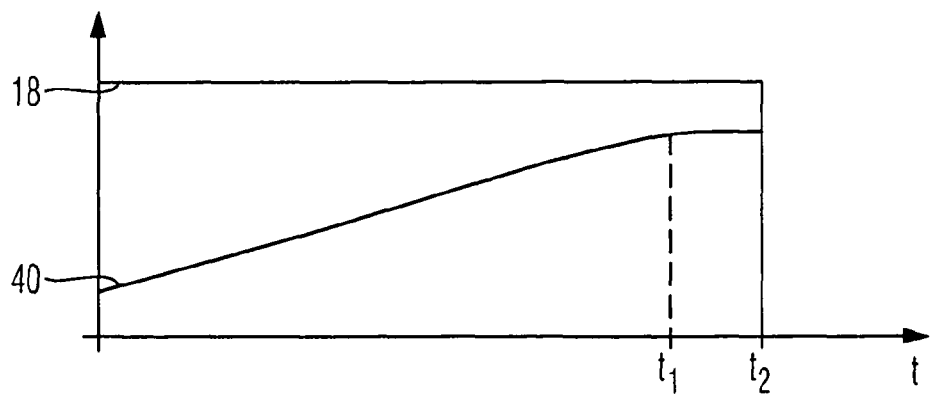
FIG. 5 shows a diagram representing a modified control of the present invention.

A modified control by the control device 26 is shown in FIG. 5. With this solution, the switch-off takes place already with a maximum of the sensor signal 40, that is, at timepoint $t_2$, and shortly after the gradient of the sensor signal has decreased.

Figure 6:
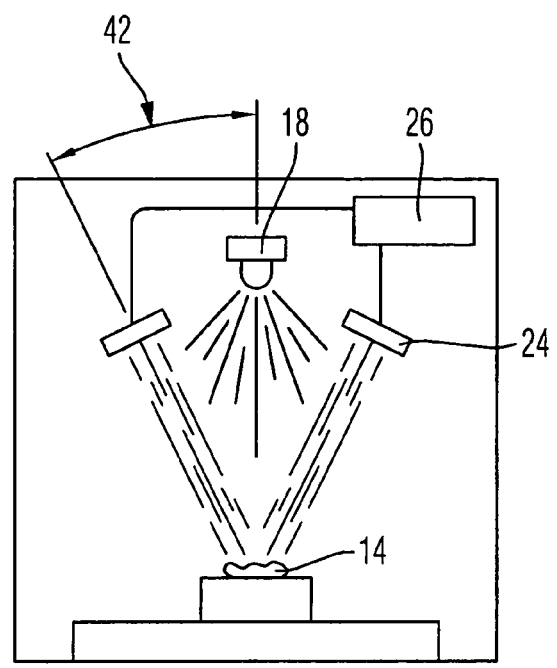
FIG. 6 shows a third embodiment of a device according to the present invention.

FIG. 6 shows a further modified embodiment of a device 10 of the present invention. With this solution, a light source 18 is arranged centrally above the dental material 14, while sensors 24 are arranged laterally and inclined at an angle above the dental material 14. An angle 42 between the optical axes of the sensors and light source can be adapted in further areas to the requirements.

Figure 7:
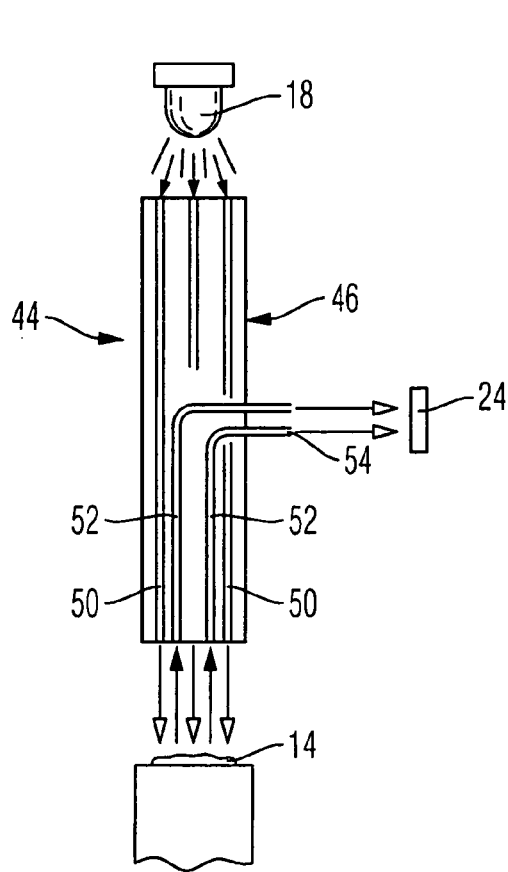
FIG. 7 shows a fourth embodiment of a device according to the present invention.
Figure 8:
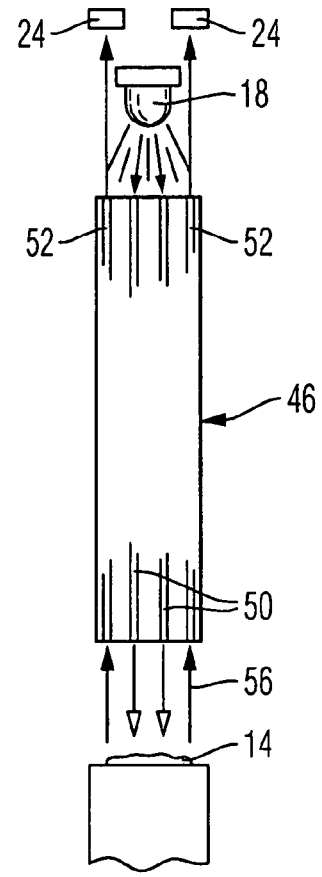
FIG. 8 shows a fifth embodiment of a device according to the present invention.

FIGS. 7 and 8 show modified embodiments of the device of the present invention, which have additional photo conducting elements. With the embodiment of FIG. 7, a photo conducting assembly 44 is provided, which has at least one optical fiber. A convex lens (not shown in FIG. 7) also is included with the photo conducting element, which collects radiation emitted from the light source 18 and conducts it to the photo conducting rod 46. Here also, in a known manner, an edge filter can be provided for screening long-wave radiation.

Figure 10:
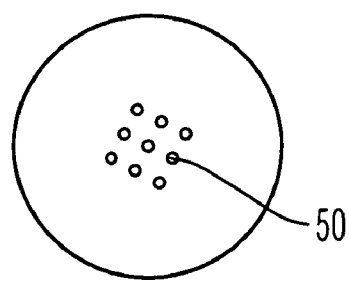
FIG. 10 shows the arrangement of the impingement-optical fibers in a photo conducting rod of the present invention.
Figure 11:
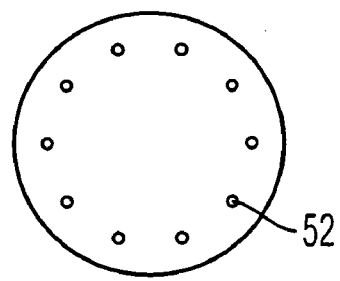
FIG. 11 shows the arrangement of the detection-optical fibers in a photo conducting rod of the present invention.

The photo conducting rod 46 comprises a plurality of adjacently arranged optical fibers (see FIGS. 10 and 11). While the impingement-optical fibers 50 extend axially through the photo conducting rod 46 and impinge the dental material 14 with light radiation, detection-optical fibers 52 are bent to the side, and indeed, into the center of the photo conducting rod 46. There, they form a light outlet 54, via which the detection radiation is conducted to the sensor 24.

Compared to the embodiment of FIG. 7, the detection-optical fibers 52 in the embodiment of FIG. 8 are completely pulled through the photo conducting rod. The detection radiation 56 in this embodiment moves accordingly from the polymerization area 14 through the photo conducting rod 46 and contacts the sensors 24, which are arranged adjacently on the outer periphery of the light conducting rod 46, but above the light source 18.

Figure 9:
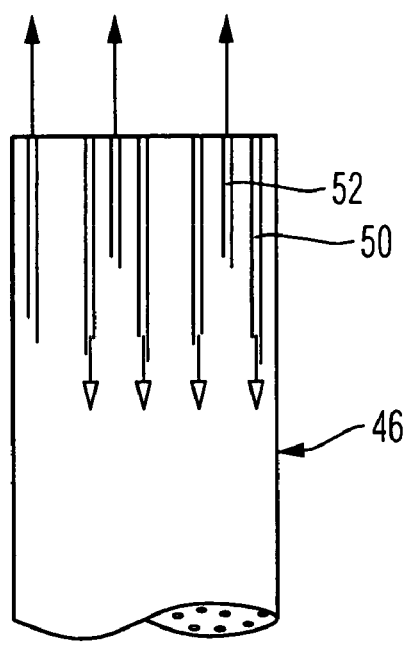
FIG. 9 shows a representation of a part of the photo conducting element of the present invention.

FIG. 9 shows how the impingement-optical fibers 50 and the detection-optical fibers 52 can run parallel to one another in the photo conducting rod. A plurality of corresponding optical fibers is provided in a suitable distribution, whereby FIGS. 10 and 11 show schematically the arrangement of the impingement-optical fibers 50 and the detection-optical fibers 52. It should be understood that the arrangement of these optical fibers in a common photo conducting rod is preferred, although, basically, also the formation of two photo conducting rods is possible.

Figure 12:
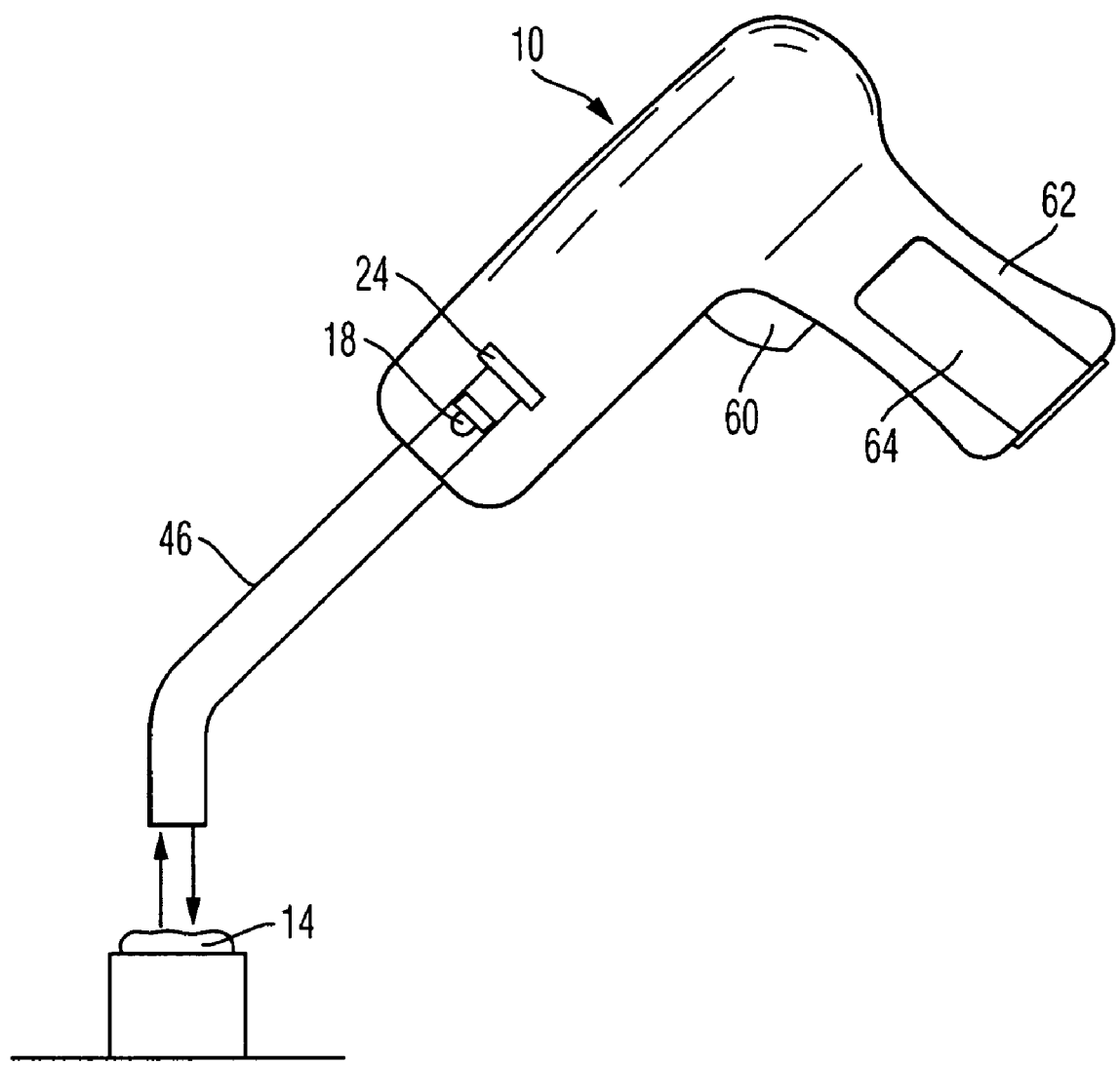
FIG. 12 shows a schematic representation of the device of the present invention as a hand-held device.

FIG. 12 shows that the device 10 of the present invention also can be realized in the form of a hand-held device. Also, with this solution, a sensor 24 is arranged above a light source 18, whereby the photo conducting rod 46 has detection- and impingement-optical fibers.

Via the offset end of the photo conducting rod, the dental material 14 can be impinged, as soon as the hand-held device 10 is switched on via the switch-on button 60. The accumulators 64 accommodated in the handle 62 of the hand-held device 20 supply the light source 18 in a known manner with energy, and the switching-off takes place as soon as it is determined in dependence on the output signal of the sensor 24 that the polymerization is completed.

The present invention is, of course, in no way restricted to the specific disclosure of the specification and drawings, but also encompasses any modifications within the scope of the appended claims.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A device for determining and controlling the degree of polymerization of polymerizable dental material (14), comprising:
   a polymerization radiation source in the form of a UV and/or violet light source and/or a near infrared heat source (18, 20) for impinging dental material (14);
   a control device (26) for the polymerization radiation source (18, 20); and
   a sensor (24) connected to the control device (26), wherein the sensor 24 detects infrared radiation emitted by the dental material during polymerization, and wherein with the sensor (24) the temperature of the detection radiation is ascertainable and from the control device (26), its temperature increase and/or decrease is capable of being evaluated.

2. The device of claim 1, wherein radiation emitted by the dental material is in a wavelength range between 800 and 10,000 nm is detectable with the sensor.

3. The device of claim 2, wherein the wavelength range of the polymerization radiation source and the detection radiation emitted from the dental material are at least fractionally different from one another.

4. The device of claim 1, wherein the optical axis of the sources (18, 20) and the sensor (24) extend in an angle deviating from zero to one another relative to the dental material.

5. The device of claim 1, further comprising multiple polymerization areas in which dental material can be polymerized, wherein one or more sensors (24) is associated with each polymerization area.

6. The device of claim 5, wherein the polymerization areas are spatially separated from one another, and wherein in each polymerization area, at least one light and/or heat source (18, 20) is disposed.

7. The device of claim 1, wherein between at least one sensor (24) and the dental material (14), at least one photo conducting assembly (44) is arranged, with which the detection radiation from the dental material area (14) can be conducted to the sensor (24) and/or with which the impingement radiation from the light and/or heat source (18, 20) can be conducted to the dental material.

8. The device of claim 7, wherein at least one optical fiber extends over a part of the entire length of a photo conducting element (46) and has a light outlet (54) facing to the side, and wherein the sensor (24) faces the light outlet.

9. The device of claim 7, wherein the photo conducting assembly (44) has at least one optical fiber (50, 52), which is penetrable in the wavelength range of 350 to 550 nm.

10. The device of claim 7, wherein the photo conducting element has at least one optical fiber, which is penetrable in the wavelength range of the detection-radiation of 800 nm to 10000 nm.

11. The device of claim 7, wherein the photo conducting element is formed as a photo conducting rod, wherein said photo conducting rod extends between the light source and the dental material.

12. The device of claim 1, wherein a photo conducting assembly (44) disposed between the dental material (14) and its polymerization area on the one hand, and the sensor (24) and/or the light and/or heat source (18, 20) on the other hand has at least one optical fiber, and wherein the at least one optical fiber extends over the entire length of the photo conducting element.

13. The device of claim 12, wherein a photo conducting element 46 has at least one optical fiber, wherein the detection radiation can be conducted with the optical fiber, and wherein the detection-optical fiber (52) is arranged in a central region or in a peripheral region of the photo conducting assembly (44).

14. The device of claim 12, wherein the photo conducting element has multiple optical fibers (50, 52), wherein with at least one optical fiber (52), the detection radiation can be conducted, and wherein the detection-optical fiber (52) is arranged in the peripheral region of the photo conducting assembly (44).

15. The device of claim 1, wherein the device (10) is formed as a hand-held unit.

16. The device of claim 1, wherein the device is connectable with an external current supply source, and/or wherein the device has an exchangeable current supply source (64).

17. The device of claim 1, wherein the light and/or heat source is formed by at least one semiconductor-energy source.

18. A device for polymerization of polymerizable dental material, comprising:
- a light and/or heat source in the form of a semi-conductor-energy source;
- a control device;
- a sensor connected to the control device, wherein the sensor detects at least one physical and/or chemical and/or biological parameter of the dental material and converts it into an electrical measurement signal.

19. The device of claim 18, wherein the sensor (24) is directed directly onto the dental material (14).

* * * * *